United States Patent [19]

Costanzi et al.

[11] Patent Number: 5,270,470
[45] Date of Patent: Dec. 14, 1993

[54] PROCESS FOR THE SYNTHESIS OF ALLYLATED DERIVATIVES OF 2,2,6,6-TETRAALKYLPIPERIDINOLS

[75] Inventors: Silvestro Costanzi, San Giuliano Milanese; Luciano Pallini, Fornovo Taro; Damiano Gussoni, Milan, all of Italy

[73] Assignee: Enichem Sintesi S.p.A., Palermo, Italy

[21] Appl. No.: 481,725

[22] Filed: Feb. 16, 1990

Related U.S. Application Data

[63] Continuation of Ser. No. 232,755, Aug. 16, 1988, abandoned, which is a continuation of Ser. No. 44,986, May 1, 1987, abandoned.

[30] Foreign Application Priority Data

May 2, 1986 [IT] Italy ................... 20296 A/86

[51] Int. Cl.$^5$ .......................................... C07D 211/36
[52] U.S. Cl. .................................................. 546/242
[58] Field of Search ........................................ 546/242

[56] References Cited

U.S. PATENT DOCUMENTS 4,684,726 8/1987 Greco et al. ................... 546/242

OTHER PUBLICATIONS

Tetrahedron Letters, vol. 27, No. 35, pp. 4171–4174 (1986).
March, J., Adv. Org. Chem., 2nd Ed., pp. 357–358 (1977).

*Primary Examiner*—Johann Richter
*Attorney, Agent, or Firm*—Shea & Gould

[57] ABSTRACT

A process is disclosed for the synthesis of 4-allyloxy-2,2,6,6-tetraalkylpiperidinic derivatives by starting from the corresponding 2,2,6,6-tetraalkylpiperidinols and from an allyl halide, characterized in that the reaction is made to take place in the absence of water, and in the presence of a finely subdivided allyl-metal hydroxide and of small amounts of a phase-transfer catalyst. The products, which are thus obtained with yields higher than 90%, are useful a stabilizers for polymers or as intermediates for such products.

17 Claims, No Drawings

PROCESS FOR THE SYNTHESIS OF ALLYLATED DERIVATIVES OF 2,2,6,6-TETRAALKYLPIPERIDINOLS

CROSS REFERENCE TO RELATED CASES

This is a continuation application of Ser. No. 07/232,755 filed Aug. 16, 1988, now abandoned, which is a continuation of Ser. No. 044,986, filed May 1, 1987, now abandoned.

The object of the present invention is a process for the synthesis of 4-aLLyLoxy-2,2,6,6-tetraaLkyLpiperidinic derivatives having the formula (I):

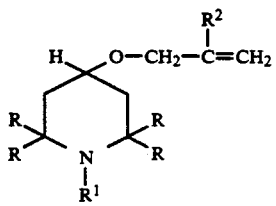

wherein the four substituents R are aLkyL groups containing from 1 to 4 carbon atoms, $R^1$ is a hydrogen atom, an aLkyL group containing from 1 to 20 carbon atoms, an aLkenyL group containing from 3 to 20 carbon atoms., a phenyLaLkyL group containing from 7 to 12 carbon atoms, or a group having the formula

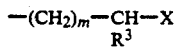

wherein m is 0, 1, 2, or 3, $R^3$ is hydrogen, methyl or phenyl and X represents a halogen atom or a cyano, —$COR^4$ —$COOR^4$, —$COSR^4$ , —$CONR^4R^5$ or —$CSNR^4R^5$ wherein $R^4$ is an aLkyL group containing from 1 to 4 carbon atoms, and $R^5$ is a hydrogen atom or a methyl group. N-substituted 2,2,6,6-tetramethyL-piperidinic derivatives bearing an aLkenyLoxy group in the 4-position, as weLL as their Use as stabilizers for synthetic polymers are claimed in the German patent application No. 2,258,752.

Compounds having the formula (I) wherein $R^1$ is a hydrogen atom are instead useful as intermediates for the stabilizer compounds of the above mentioned German patent application No. 2,258,752, as well as for further stabilizers, such as, e.g., those as disclosed in U.S. VXR patent application Nit. 733, 526 filed on May 13, 1985.

In the German patent application No. 2,258,752 the preparation is disclosed of 4-allyloxy-l-allyl-2,2,6,6-tetramethylpiperidine by means of the N-allylation with allyl bromide of 4-allyloxy-2,2,6,6-tetramethylpiperidine. The reaction leads, besides to the desired product, to the formation of 4-allyloxy-2,2,6,6-tetramethylpiperidine hydrobromide too, wherein the starting compound acts as the acceptor of the hydrobromic acid which is formed during the reaction, the yields thereof being thus halved.

The preparation of 4-allyloxy-2,2,6,6-tetramethylpiperidine by O-allylation of 2,2,6,6-tetramethylpiperidinol is disclosed on the contrary in U.S. patent application No. 733,526 and, in particular, in Example 1 thereof. In such Example, the alcoholic hydroxyl of piperidine is etherified with allyl halides according to the so-called Williamson's synthesis, which precisely provides the synthesis of ethers by passing through the intermediate formation of the corresponding alkoxides.

But such a synthesis appears to be not convenient from an industrial standpoint, in as much as for it a two-step process must be in fact provided, wherein the alkoxide intermediate is first formed, and is subsequently converted into the Allyl ether by the addition of allyl halides. Furthermore, as reported in the cited patent application, the yields supplied by this reaction are lower than 70%.

The application is known as well to the Williamson's synthesis of the phase-transfer technique, according to which the halide is reacted with the alcohol in 50% aqueous solution of KOH or NAOH, and in the presence of a phase transfer catalyst, thus the desired unsymmetrical ether being obtained. In this particular case, such a reaction suffers anyway from the disadvantage that it also leads to the formation of allyl alcohol, and, hence, of diallyl ether, thus the reaction yields, as computed relatively to the allyl halide, being reduced under 70%.

Is has been surprisingly found now that by reacting a piperidinic derivative having the formula (II):

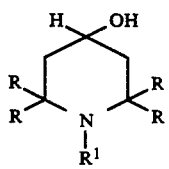

wherein R and $R^1$ have the above-defined meanings, with an at least equimolar amount of a allyl halide of formula (III)

$$CH_2=CR^2-CH_2Y \qquad (iii)$$

wherein $R^2$ is hydrogen or methyl, and Y is a chlorine or bromine atom, in the presence of an at least equimolar amount of a finely subdivided alkaline hydroxide and of catalytic amounts of a phase-transfer catalyst, in the absence of solvents, or in the presence of an inert organic solvent, the desired unsymmetrical ether of formula (I) is obtained with yields close to, or higher than, 90%, relatively to both of the starting products.

Although the reaction proceeds well even when equimolar amounts are used of the allyl halide of formula (III), in general the use of a large excess of such a reactant is preferred. This allows indeed the use of a further solvent to be avoided, without other types of problems being generated, in that unreacted allyl halide can be easity distilled off at reaction end, and recycled.

According to a preferred practical embodiment of the present invention, the reaction is carried out by using an excess of the allyl halide (III) comprised within the range of from 100 to 400% by mot, relatively to the stoichiometric amount. Also as regards the alkaline hydroxide, even if an equimolar amount thereof according to the reaction stoichiometry, is enough, better resuits are obtained by using an excess thereof.

Optimum resuits were obtained in particular by using the alkaline hydroxide in an excess comprised within the range of from 30 to 150% by mot, relatively to the stoichiometric amount. Preferred alkaline hydroxides will be, due to obvious reasons of availability and cheapness, sodium hydroxide and potassium hydroxide.

The reaction requires also the presence of catalytic amounts of a phase-transfer catalyst, which can be selected from the quaternary ammonium salts and the crown ethers.

The obtainment of the best results, both in terms of yields and of lower cost, make the quaternary ammonium hydroxides be preferered; among them, in particular tetrabutylammonium iodide, bromide, chloride and sulphate, benzyltriethylammonium chloride, tetrapropylammonium bromide and trimethylhexadecylammonium fluoride have shown to be particularly satisfactory.

The phase-transfer catalyst is generally used at percentages comprised within the range of from 0.005 to 2%, and preferably of from 0.1 to 0.5% by mot, relatively to the piperidinic substrate of formula (II) used as the starting product.

As already seen, the reaction can be carried out in the absence of solvents, in particular when a large excess of the allyl halide is used, or in the presence of a suitable polar, aprotic organic solvent which does not interfere negatively during the reaction course.

Suitable organic solvents are, e.g., the alkyl ethers, such as methyl-tert-butyl ether, diisopropyl ether, diisobutyl ether, dimethoxyethane, and so forth; the cyclic ethers, such as dioxane and tetrahydrofuran, and still further analogous solvents.

The O-allylation reaction of the present invention is generally carried out at a temperature comprised within the range of from 20° C. to 120° C. Although the reaction may proceed also at room temperature, in general it is preferred to accelerate the rate thereof by operating at the reaction mixture reflux temperature. In general, the reaction is complete, according to the temperature it is carried out at, within a time range of from 1 to 24 hours. At reaction end, the desired product of formula (I) is recovered, by using conventional techniques which will be immediately evident to anyone skilled in the chemical art.

A convenient method provides, e.g., the addition, to the reaction mixture, of water, and of an organic solvent immiscible with water,, e.g., benzene, toluene, xylene, anisole, heptane, cyclohexane, etc., the separation of the organic phase, and the removal from this of the solvent and of the unreacted allyl halide, followed, if desired, by the possible purification of the so-obtained residue, by distillation under reduced pressure.

group containing from 1 to 20 carbon atoms, an alkenyl group containing from 3 to 20 carbon atoms, or a phenylalkyl group containing from 7 to 12 carbon atoms, and $R^2$ is either hydrogen or methyl.

To the purposes of the present Applicant, a more preferred practical embodiment of the present invention is represented by the use of the new process for the preparation of piperidinic derivatives of formula (I), wherein the four R substituents are methyl, $R^1$ is a hydrogen atom, an alkyl group containing from 1 to 20 carbon atoms or an alkenyl group containing from 3 to 20 carbon atoms, and $R^2$ is either hydrogen or methyl.

The following Examples disclose in greater detail some representative aspects of the process of the present invention, and in no way should they be regarded as being limitative of the scope of said invention.

EXAMPLE 1

Preparation of 4-allyloxy-2,2,6,6-tetramethylpiperidine

To a 3-neck 500-ml flask, equipped with mechanical stirrer, reflux condenser and thermometer, 2,2,6,6-tetramethyl-piperidin-4-ol (62 g; 0.395 moo, NAOH powder (31 g; 0.775 moo, allyl chloride (100 g, 1.317 mot) and tetrabutylammonium iodide (0.4 g; 0.001 mot) are charged. The mixture, strongly stirred, is kept heated at reflux temperature about 6 hours. It is then cooted to room temperature, and to it H 20 (150 mi) and toluene (115 mi) are added.

The organic phase is separated and submitted to distillation under atmospheric pressure, with, besides the toluene used, the excess of allyl chloride (66 g) being recovered.

4-Allyloxy-2,2,6,6-tetramethylpiperidine, purified by distillation of the residue (b.p. 64°-65° C. (1 mm$_{Hg}$) was characterized by I.R., N.M.R. and mass spectroscopy. The reaction yield computed relatively to charged 2,2,6,6-tetramethylpiperidinol resuited of 73%, and the yield retative to allyl chloride, with the chloride recovered on distillation being considered recyclable, resuited of 88%.

EXAMPLES 2 TO 6

Examples 2-6 were carried out as reported in Example 1, but using different phase-transfer catalysts, in the same amount, by mot, relatively to the substrate (piperidinol mol/catalyst mol =about 400). The experimental resuits are reported in the following Table.

| Example No. | Catalyst | Piperidinol % Conversion | Piperidinol % Selectivity | Allyl Chloride % Selectivity |
|---|---|---|---|---|
| 2 | Tetrabutylammonium Chloride (TBAC) | 93 | 98 | 87 |
| 3 | Tetrabutylammonium Bromide (TBAB) | 97 | 97 | 90 |
| 4 | Tetrapropylammonium Bromide (TPAB) | 95 | 97 | 88 |
| 5 | Hexadecyltrimethylammonium Fluoride (ETAF) | 85 | 91 | 75 |
| 6 | Crown Ether 18.6 | 73 | 90 | 81 |

The compounds obtained by means of the process of the present invention are useful as stabilizers for polymers, or as intermediates for the preparation of stabilizers for polymers.

On considering that, a preferred form of practical embodiment of the present invention provides the use of the new process for the preparation of piperidinic derivatives of formula (I), wherein the four R groups represent a methyl group, $R^1$ is a hydrogen atoms, an alkyl

EXAMPLES 7 TO 9

The following Examples were carried out by substantially following the method as disclosed in Example 1, and using the compounds listed in the following Table, in the "Substrate" headed column, instead of 2,2,6,6-tetramethylpiperidinol. The catalyst and the amounts used are shown in the Table. The corresponding allylethers obtained were characterized by I.R., N.M.R. and mass spectroscopy.

| Example No. | Substrate | Catalyst | Substrate Mol / Catalyst Mol | % Yield Relatively to the Substrate | Allyl Chloride % Selectivity | Product B.p. (°C.) |
|---|---|---|---|---|---|---|
| 7 | H₂=CH—CH₂—N(piperidine with Me,Me,Me,Me)—OH | TBAB | 500 | 92 | 94 | 92-3 (0.4 mm_Hg) |
| 8 | CH₃—N(piperidine with Me,Me,Me,Me)—OH | TBAB | 400 | 93 | 93 | 116-8 (12 mm_Hg) |
| 9 | C₆H₅—CH₂—N(piperidine with Me,Me,Me,Me)—OH | TBAB | 200 | 83 | 87 | 115-20 (1 mm_Hg) |

EXAMPLES 10 TO 17

The following Examples report the influence of the base nature and amount on the yield, as referred to 2,2,6,6-tetramethylpiperidinol. The reactions were carried out according to as reported in Example 1, by using TBAB as the catalyst (substrate mol/catalyst mot The reaction time is 6 hours.

| Example No. | Base | Substrate Mol/ Base Mol | Yield Relatively to the Substrate |
|---|---|---|---|
| 10 | NaOH | 0.3 | 95 |
| 11 | NaOH | 0.4 | 91 |
| 12 | NaOH | 0.54 | 93 |
| 13 | NaOH | 0.6 | 93 |
| 14* | NaOH | 0.8 | 82 |
| 15 | K₂CO₃ | 0.6 | 10 |
| 16 | NaHCO₃ | 0.6 | 10 |
| 17 | Ca(OH)₂ | 0.6 | 10 |

*By prolonging the reaction times (beyond 12 hours), also in this case a yield higher than 90% is obtained.

EXAMPLES 18-20

In the following Table the resuits are reported, which were obtained by carrying out the reaction substantially as disclosed in Example 1, but using TBAB as the catalyst, and varying the molar ratio thereof relatively to the substrate. The yields of allyloxypiperidine were measured after a 3-hour reaction time at refluxing temperature.

| Example No. | Piperidinol Mol/ Catalyst Mol | Yield % |
|---|---|---|
| 18 | 160 | 99.5 |
| 19 | 360 | 89 |
| 20 | 1075 | 56 |

EXAMPLES 21 TO 23

The reactions of the following examples were carried out by operating according to the known art of the phase transfer, by using a concentrated aqueous solution of NaOH. The reactions were carried out with 2,2,6,6-tetramethylpiperidinol as the substrate, and TBAB as the catalyst (piperidinol mol/TBAB mol =50).

| Example No. | Substrate Weight H₂O Weight | Substrate Weight NaOH Weight | Piperidinol % Yield | Allyl Chloride % Selectivity | Reaction Time (hours) |
|---|---|---|---|---|---|
| 21 | 0.5 | 0.5 | 94 | 70 | 2 |
| 22 | 1 | 1 | 95 | 71 | 3 |
| 23 | 0.5 | 1 | 86 | 68 | 3 |

EXAMPLE 24

Preparation of 4-[(2-methyl-2-propenyl)-oxy]-2,2,6,6-tetramethylpiperidine

Substantially following the same procedure as of Example 1, but using 3-chloro-2-methylpropene (119 g, 1.3 mot) instead of allyl chloride, the compound of the title is obtained with a yield of 92% relatively to charged piperidinol, and a selectivity higher than 98% (b.p. 50° C./0.2 mm_Hg).

We claim:

1. A process for the synthesis of a 4-allyloxy-2,2,6,6-tetraalkylpiperidinic derivative having the formula (I):

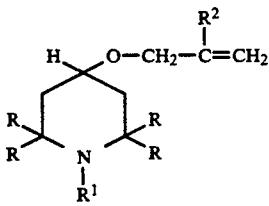

wherein the four substituents R are alkyl groups containing from 1 to 4 carbon atoms, $R^1$ is a hydrogen atom, an alkyl group containing from 1 to 20 carbon atoms, a phenylalkyl group containing from 7 to 12 carbon atoms, or a group having the formula

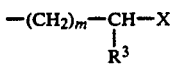

wherein m is 0, 1, 2, or 3, $R^3$ is hydrogen, methyl or phenyl and X represents a halogen atom or a cyano, —$COR^4$, —$COOR^4$, —$COSR^4$, —$CONR^4R^5$, or —$CSNR^4R^5$ group, wherein $R^4$ is an alkyl group containing from 1 to 4 carbon atoms, and $R^5$ is a hydrogen atom or an alkyl group containing from 1 to 4 carbon atoms, and $R^2$ is either hydrogen or a methyl group, by the allylation of a piperidinol having the formula (II):

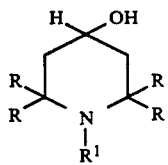

wherein R and $R^1$ have the above-defined meanings, with an allyl halide of formula (III)

$$CH_2=CR^2-CH_2Y \qquad (III)$$

wherein $R^2$ is as defined above, and Y is a chlorine or bromine atom, comprising: contacting the piperidinic derivative of formula (II) with an at least equimolar amount of the allyl halide in the presence of an at least equimolar amount of a finely subdivided alkaline hydroxide and of catalytic amounts of a phase-transfer catalyst, in the absence of water.

2. The process according to claim 1, wherein the piperidinic derivative of formula (II) is contacted with an excess of the allyl halide.

3. The process according to claim 2, wherein the allyl halide is in excess of from 100 to 400% by mol, relative to the stoichiometric amount.

4. The process according to claim 1, wherein the process is conducted in an excess of alkaline hydroxide.

5. The process according to claim 4, wherein the alkaline hydroxide is in excess of from 50 to 150% by mol relative to the stoichiometric amount.

6. The process according to claim 1, wherein the phase-transfer catalyst is a quaternary ammonium salt.

7. The process according to claim 6, wherein the quaternary ammonium salt is a tetraalkylammonium halide.

8. The process according to claim 7, wherein the tetraalkylammonium halide is tetrabutylammonium bromide.

9. The process according to claim 1, wherein the amount of the phase-transfer catalyst is from 0.005 to 2% by mol relative to the piperidinic derivative of formula (II).

10. The process according to claim 9, wherein the amount of the phase-transfer catalyst is from 0.2 to 0.4% by mol relative to the piperidinic derivative of formula (II).

11. The process according to claim 1, wherein the process is conducted in the absence of solvents.

12. The process according to claim 1, further comprising conducting the process in the presence of an inert organic solvent selected from group consisting of alkyl ethers and cyclinc ethers.

13. The process according to claim 1, wherein the alkaline hydroxide is selected from the group consisting of sodium hydroxide and potassium hydroxide.

14. The process according to claim 1, wherein the process is conducted at a temperature of from 20° to 120° C.

15. The process according to claim 14, wherein the process is carried out at the reflux temperature of the reaction mixture.

16. The process according to claim 1, wherein R is methyl, $R^1$ is a hydrogen atom, an alkyl group containing from 1 to 20 carbon atoms, an alkenyl group containing from 3 to 20 carbon atoms, or a phenylalkyl group containing from 7 to 12 carbon atoms, and $R^2$ is hydrogen or methyl.

17. The process according to claim 16, wherein $R^1$ is a hydrogen atom, an alkyl group containing from 1 to 20 carbon atoms, or an alkenyl group containing from 3 to 20 carbon atoms.

* * * * *